(12) United States Patent
Gemmel et al.

(10) Patent No.: US 10,842,456 B2
(45) Date of Patent: Nov. 24, 2020

(54) TOMOSYNTHESIS METHOD AND XRAY RECORDING APPARATUS

(71) Applicant: Siemens Healthcare GmbH, Erlangen (DE)

(72) Inventors: Alexander Gemmel, Erlangen (DE); Gerhard Kleinszig, Forchheim (DE); Björn Kreher, Bräuningshof (DE); Benedict Swartman, Mannheim (DE); Wei Wei, Forchheim (DE); Markus Weiten, Nuremberg (DE); Qiao Yang, Fürth (DE)

(73) Assignee: Siemens Healthcare GmbH, Erlangen (DE)

(*) Notice: Subject to any disclaimer, the term of this patent is extended or adjusted under 35 U.S.C. 154(b) by 23 days.

(21) Appl. No.: 16/163,357

(22) Filed: Oct. 17, 2018

(65) Prior Publication Data
US 2019/0117180 A1 Apr. 25, 2019

(30) Foreign Application Priority Data

Oct. 19, 2017 (EP) ..................... 17197323
Aug. 16, 2018 (EP) ..................... 18189341

(51) Int. Cl.
*A61B 5/00* (2006.01)
*A61B 6/00* (2006.01)
(Continued)

(52) U.S. Cl.
CPC .............. *A61B 6/505* (2013.01); *A61B 6/025* (2013.01); *A61B 6/027* (2013.01); *A61B 6/0487* (2020.08);
(Continued)

(58) Field of Classification Search
CPC .. A61B 5/00; A61B 6/00; A61B 6/505; A61B 6/0487; A61B 6/025; A61B 6/027;
(Continued)

(56) References Cited

U.S. PATENT DOCUMENTS 7,453,976 B1 * 11/2008 Yin ..................... A61B 6/032
378/65
7,460,637 B2 * 12/2008 Clinthorne ............... A61B 6/14
378/17

(Continued)

FOREIGN PATENT DOCUMENTS

| DE | 102006048451 A1 | 4/2008 |
|---|---|---|
| DE | 102007034221 A1 | 4/2008 |
| DE | 102015201067 A1 | 7/2016 |
| DE | 102015207727 A1 | 11/2016 |
| WO | WO2009153789 A1 | 12/2009 |

OTHER PUBLICATIONS

European Search Report for European Patent Application No. 18189341.3-1124 dated Mar. 20, 2019.

*Primary Examiner* — Ali Bayat
(74) *Attorney, Agent, or Firm* — Lempia Summerfield Katz LLC

(57) ABSTRACT

A method for determining an alignment between at least two bone parts of an elongated bone system of a patient includes recording a plurality of partially spatially overlapping projection images by a recording system of an x-ray device during a translational movement of the x-ray device or the recording system in a direction of or parallel to a longitudinal axis of the bone system. Tomosynthesis image data of the bone parts is reconstructed from the recorded projection images, and an alignment angle between the at least two bone parts is determined or estimated at least partially based on the reconstructed tomosynthesis image data and/or the plurality of projection images.

20 Claims, 5 Drawing Sheets

(51) Int. Cl.
*A61B 6/02* (2006.01)
*A61B 6/04* (2006.01)
*A61B 6/12* (2006.01)

(52) U.S. Cl.
CPC .......... *A61B 6/4441* (2013.01); *A61B 6/5217* (2013.01); *A61B 6/5241* (2013.01); *A61B 6/542* (2013.01); *A61B 5/4504* (2013.01); *A61B 5/7271* (2013.01); *A61B 6/12* (2013.01); *A61B 6/5205* (2013.01); *A61B 6/54* (2013.01)

(58) Field of Classification Search
CPC ... A61B 6/4441; A61B 6/5217; A61B 6/5241; A61B 6/542; A61B 6/12; A61B 6/5205; A61B 6/54; A61B 5/4504; A61B 5/7271
USPC ........................................................ 382/132
See application file for complete search history.

(56) References Cited

U.S. PATENT DOCUMENTS

| | | | |
|---|---|---|---|
| 2008/0077003 A1 | 3/2008 | Barth | |
| 2011/0188726 A1 | 8/2011 | Nathaniel | |
| 2012/0134464 A1* | 5/2012 | Hoernig | A61B 6/481 378/22 |
| 2012/0257714 A1 | 10/2012 | Graumann | |
| 2013/0101082 A1* | 4/2013 | Jordan | A61B 6/482 378/19 |
| 2016/0213343 A1 | 7/2016 | Barth et al. | |
| 2016/0242703 A1* | 8/2016 | Sadakane | A61B 6/4441 |
| 2016/0317104 A1* | 11/2016 | Guez | A61B 6/486 |
| 2016/0321807 A1 | 11/2016 | Wiets | |
| 2019/0320995 A1* | 10/2019 | Amiri | A61B 6/463 |

\* cited by examiner

FIG 1
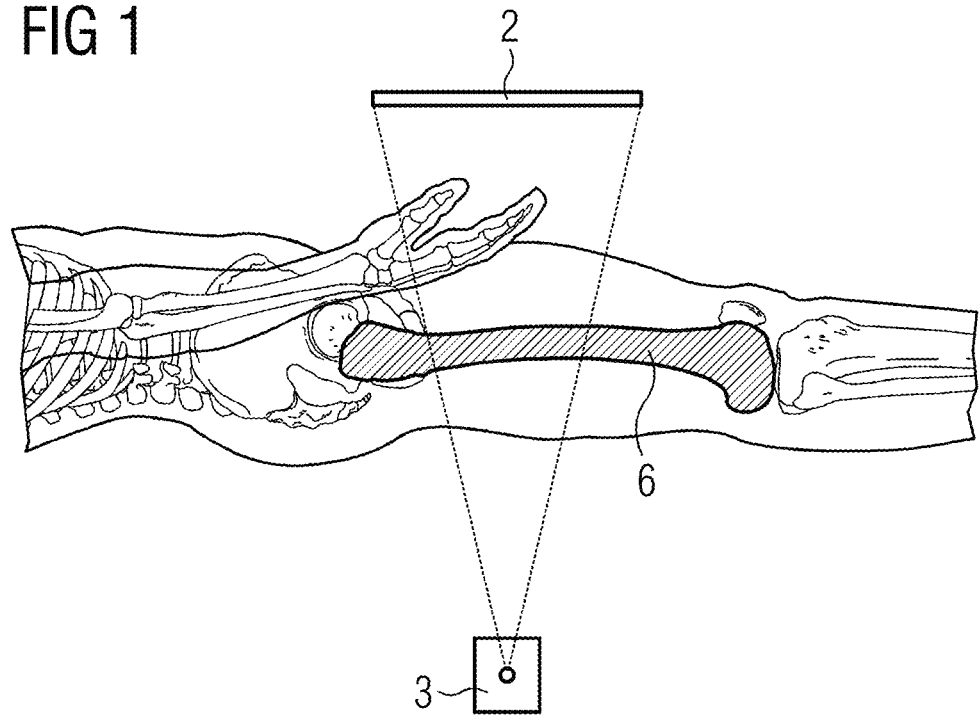
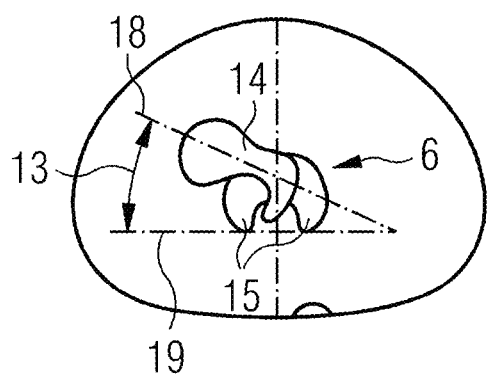
FIG 2
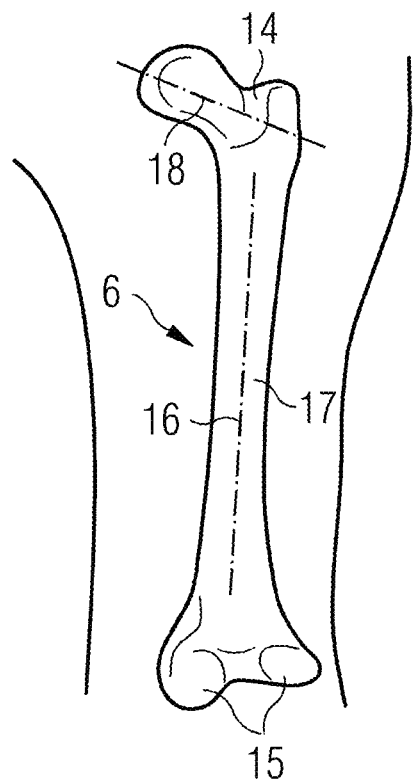
FIG 3

TOMOSYNTHESIS METHOD AND XRAY RECORDING APPARATUS

This application claims the benefit of EP 17197323.3, filed on Oct. 19, 2017, and EP 18189341.3, filed on Aug. 16, 2018, which are hereby incorporated by reference in their entirety.

BACKGROUND

The present embodiments relate to determining an alignment between at least two bone parts of a patient.

Femur neck fractures occur relatively frequently and, in most instances, are to be treated surgically. With this surgical intervention, a femoral nail is generally introduced into the femoral neck. Prior to locking the femoral nail, the antitorsion angle is to be aligned between the distal and the proximal end of the femur. Since the determination of the antitorsion angle during the surgical intervention is very complicated, in most instances, the antitorsion angle is quantified inadequately. The alignment is determined based on instinct or by the physician comparing the right and left foot positions. Deviations in the antitorsion angle by +/−12° are the rule. As a result of this, frequent complaints and rapid wear of the joint surfaces (e.g., arthrosis) result.

DE 10 2015 201 067 A1 discloses a method for determining an antitorsion angle with simple two-dimensional x-ray images.

The following facts are also considered to be challenges when determining the antitorsion angle: (a) The angle is to be determined between the distal and the proximal end of the femur, and a large field of view is therefore to be provided. The length of the femur is approximately 50 cm in adults, for example. (b) Since a rotation along the axis of the bone is to be determined, simple projection images are not adequate. Previously the determination of the angle could only be quantified with sufficient accuracy in one volume image (MPR). (c) The alignment is to be carried out during the surgical intervention, and as a result, further challenges arise with respect to sterility, time constraints, and patient immobility.

Currently, no standardized methods are known for quantifying the antitorsion angle during an operative intervention.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that eliminates the cited disadvantages is provided. As another example, an x-ray recording apparatus suited to carrying out the method is provided.

The method of one or more of the present embodiments for determining an alignment between at least two bone parts of an elongated bone system of a patient includes recording a plurality of partially spatially overlapping projection images by a recording system of an x-ray device (e.g., a mobile x-ray device) during a translational movement of the x-ray device or the recording system in a direction of or parallel to a longitudinal axis of the bone system. Tomosynthesis image data (e.g., slice images) of the bone parts is reconstructed from the recorded projection images, and an alignment angle between the at least two bone parts is determined or estimated at least partially with the aid of the projection images or the reconstructed tomosynthesis image data.

The method of one or more of the present embodiments eliminates the problems that occur when an alignment angle (e.g., antitorsion angle) of an elongated bone system (e.g., femur) is determined. The translational movement of the mobile x-ray device allows a particularly "long" field of view to be mapped. The length of the slice volume resulting, if required, may be determined, if required, by the length of the path traveled. This length may be defined by the operating physician, for example. The tomosynthesis enables not only two-dimensional images to be recorded, but also allows three-dimensional slice images or three-dimensional partial images (e.g., volume representations) to be recorded and reconstructed. Using these three-dimensional slice images or partial images, quantification of the alignment angle (e.g., antitorsion angle) is easily possible and with good quality. For example, a mobile x-ray device may also be used in a sterile environment (e.g., during an operation). The translational movement of the mobile x-ray device may be achieved by a very quick, simple, and low-cost workflow. The requisite dose of radiation is significantly lower for a tomosynthesis recording than for conventional volume scans such as CT or DynaCT.

Using the method, the antitorsion angle may be determined during a surgical intervention, for example, before a requisite femoral nail is locked, so that a correction is enabled when an inconsistent antitorsion angle is defined. Within the scope of the correction, the distal and the proximal end of the femur may then be aligned more accurately with respect to one another. The correction option results in improved operation results and fewer complications and complaints from the patient.

The determination or estimation of the alignment angle is carried out at least partially based on reconstructed tomosynthesis image data (e.g., of a reconstructed slice image or reconstructed partial images or image cutouts). In the presence of a slice image or partial images or image cutouts that are registered with respect to one another, two bone parts of the elongated bone system may be identified by segmentation or object recognition. Subsequently, the alignment angle occurring between the two bone parts may be determined or estimated, for example, by applying axes or tangents to the relevant structures of the at least two bone parts. The result may then be output by a display apparatus, for example. The antitorsion angle is the angle between the femoral neck and the femoral condyle (e.g., more precisely, the angle that is formed by a femoral neck axis and a femoral condyle tangent). In the presence of a three-dimensional slice image, such as is produced in the present method, the antitorsion angle may be easily determined.

Alternatively to a femur and an antitorsion angle, the elongated bone system involving a spinal column segment and the alignment angle may also be formed by an angle between two vertebral bodies. Spinal column injuries occur in almost 28% of all severely injured patients in Germany. Considered statistically, the lower cervical vertebra is affected in every 6th patient. Since these interventions are very challenging, during the intervention, the surgeon is reliant on imaging methods. However, the intraoperative 2D imaging such as the conventional radiography in the cervicothoracic region is limited on account of significant overlapping of the shoulders, and an adequately precise representation of a repositioning result of the spinal column is only possible with a 3D imaging. All problems may also be easily resolved by, for example, the method of one or more of the present embodiments. The elongated region of interest as a three-dimensional slice image or cutouts therefrom may be shown quickly and easily in the operating room as 3D partial images, where the radiation exposure to the patient remains minimal. If a non-optimal angle between, for example, two spinal columns is determined or defined, a further intervention may be carried out for correction purposes.

According to a further embodiment, the alignment angle between the at least two bone parts is determined or estimated exclusively based on reconstructed tomosynthesis image data (e.g., slice images).

According to a further embodiment, further projection images from different projection directions (e.g., lateral projection images) are used to determine or estimate the alignment angle between the at least two bone parts.

According to a further embodiment, a rotational movement of the recording system is additionally carried out during the recording and the translational movement of the x-ray device. The 3D imaging may be improved significantly by this. A rotation of, for example, 60° (e.g., rotational angle of +30° to −30°) may be provided here.

According to one embodiment, the distance between two images of the plurality of partially spatially overlapping images is constant and smaller than or equal to half of the object width (d') that may be detected by an opening angle α of an x-ray source of the recording system. A consistent image quality of the slice images is achieved across the entire recorded length by the constant distance. A distance of less than or equal to half of the detectable object width d' supplies sufficient depth information for a high-quality three-dimensional slice image. The detectable object width d' is the cutout from the elongated bone system that may be projected at most onto the actual detector width d of the x-ray detector of the recording system. The relation $$d' = d\frac{SOD}{SID}$$

is valid, where source object distance (SOD) is the distance between the object and the x-ray source and source image distance (SID) is the distance between the x-ray source and the x-ray detector of the recording system.

According to a further embodiment, the distance between each two images of the plurality of partially spatially overlapping images differs as a function of a recording position along the elongated bone system. Provision may be made in the case of a femur, for example, for the distance in the central region of the elongated bone system (e.g., the femoral shaft) to be higher and the image quality to thus be lower, since no relevant regions are present for the determination of the antitorsion angle. Provision may also be made with other elongated bone systems for the distance in the region of a fracture or in the contact region of the two bone parts to be smaller and a higher image quality therefore to be achieved there.

According to a further embodiment, the translational movement is carried out by, for example, automatically controlled rollers of the mobile x-ray device along a floor. The motorized rollers or wheels may be controlled by the system controller. Alternatively, a fixedly installed x-ray device may be moved on rails, or only the recording system (e.g., C-arm) of a fixedly installed x-ray device may be moved translationally on suspension.

One or more of the present embodiments include an x-ray recording apparatus for carrying out the method. The x-ray recording apparatus is configured as a mobile C-arm x-ray device having a recording system that is held on a C-arm with an x-ray source and an x-ray detector. A system controller controls the recording of a plurality of partially spatially overlapping images (e.g., tomosynthesis image data) by the recording system during a translational movement of the recording system of the x-ray device. An image processing unit (e.g., an image processor) and a calculation unit (e.g., a calculator; the image processor or another processor) reconstructs slice images and determines the alignment angle. The x-ray recording apparatus has a trolley that may move automatically on rollers and on which the C-arm is arranged.

BRIEF DESCRIPTION OF THE DRAWINGS

FIG. 1 shows a known recording system for recording a femoral cutout;

FIG. 2 shows a sectional view of a known antitorsion angle;

FIG. 3 shows a top view of a known antitorsion angle;

DETAILED DESCRIPTION

Figure 4:
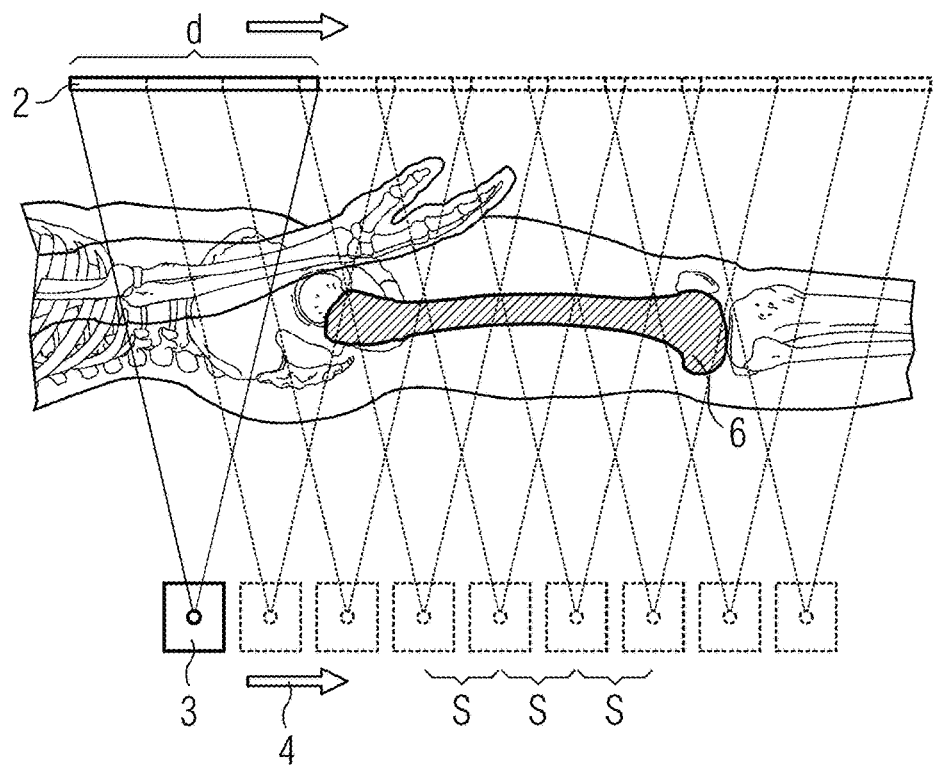
FIG. 4 shows one embodiment of a recording system for recording a plurality of partially spatially overlapping images for displaying a femur.

A known recording system with an x-ray detector 2 and an x-ray source 3 for recording a two-dimensional x-ray image of a femur is shown in FIG. 1. It is possible determine an antitorsion angle after a fracture and during an OP for correcting the femur 6 to a very limited extent using an image of this type. A volume may be acquired at a distal end of the femur, and a volume may be acquired at a proximal end of the femur with the aid of mobile 3D-capable x-ray devices. Based on the complex workflow and the high radiation dose applied, this is not carried out, however, and would also not result in an optimal determination of the antitorsion angle, since two independent volumes are to be evaluated.

A known antitorsion angle 13 is shown as a sectional image and as a top view in FIGS. 2 and 3, respectively. This is the angle between the femoral neck 14 and the femoral condyle 15 (e.g., more precisely, the angle that is formed by the femoral neck axis 7 and the femoral condyle tangent 19). Following a fracture of the femur 6 and an incomplete correction, the femoral neck 14 and the femoral condyle 15 are frequently arranged twisted toward each other along the femoral shaft axis 16 of the femoral shaft 17.

FIG. 4 shows a recording system for recording a plurality of partially spatially overlapping images for displaying a femur. For this purpose, the recording system is moved essentially in a direction 4 of the elongated bone system (e.g., the femoral shaft axis of the femur) or parallel hereto in a translational movement, and x-ray images are recorded at generally regular intervals during the movement of the recording system. The sequence of movement is shown as, for example, a plurality of x-ray source 3-x-ray detector 2 combinations. In the positions shown, the respective x-ray images are recorded. The source distance s is the distance between two x-ray images. On the assumption that the source object distance (SOD) (e.g., distance between the x-ray source and the recording object; elongated bone system) remains constant along the traveled trajectory, the detectable object width corresponds to d'=d*SOD/SID, where d is the actual detector width, for a specific source-image distance (SID) (e.g., distance between x-ray detector and x-ray source).

Figure 5:
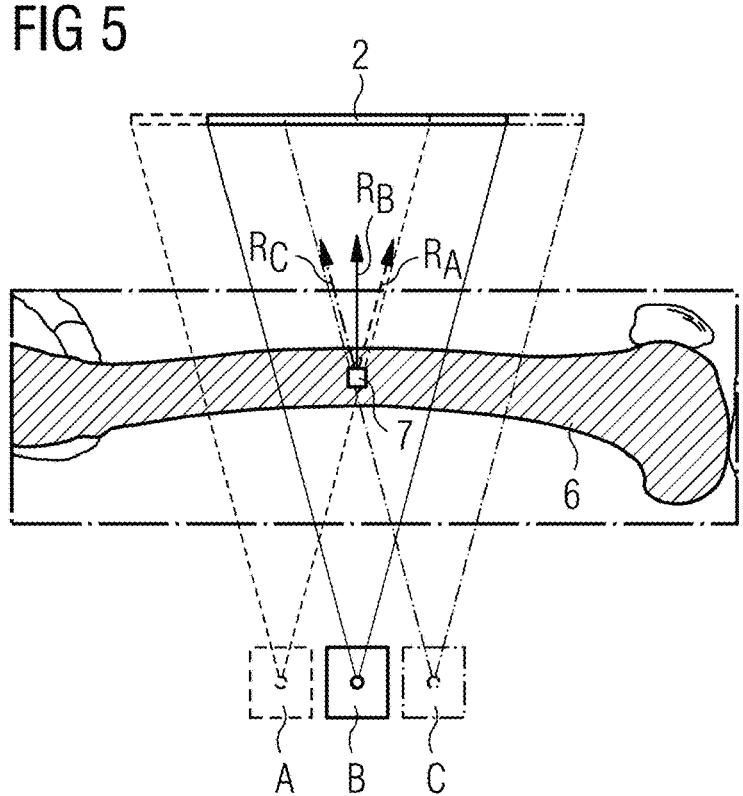
FIG. 5 shows an enlarged view of the recording geometry according to FIG. 4 with three different projection directions for reconstructing a slice image.

A cutout from the diagram in FIG. 4 is shown in FIG. 5, where the geometry of three successive x-ray images is shown. On account of the geometry, spatial points 7 that are fully passed over are shown in the x-ray images from different projection directions. This may be used to reconstruct a slice image of the completely passed-over region with the aid of a tomosynthesis method. In a first position A of the recording system, the spatial point 7 is mapped from the first projection direction $R_A$; in a second position B of the recording system, the spatial point 7 is mapped from the second projection direction $R_B$; and in a third position C of the recording system, the spatial point 7 is mapped from the third projection direction $R_C$. This is used to reconstruct a slice image with the aid of a tomosynthesis method.

Figure 6:
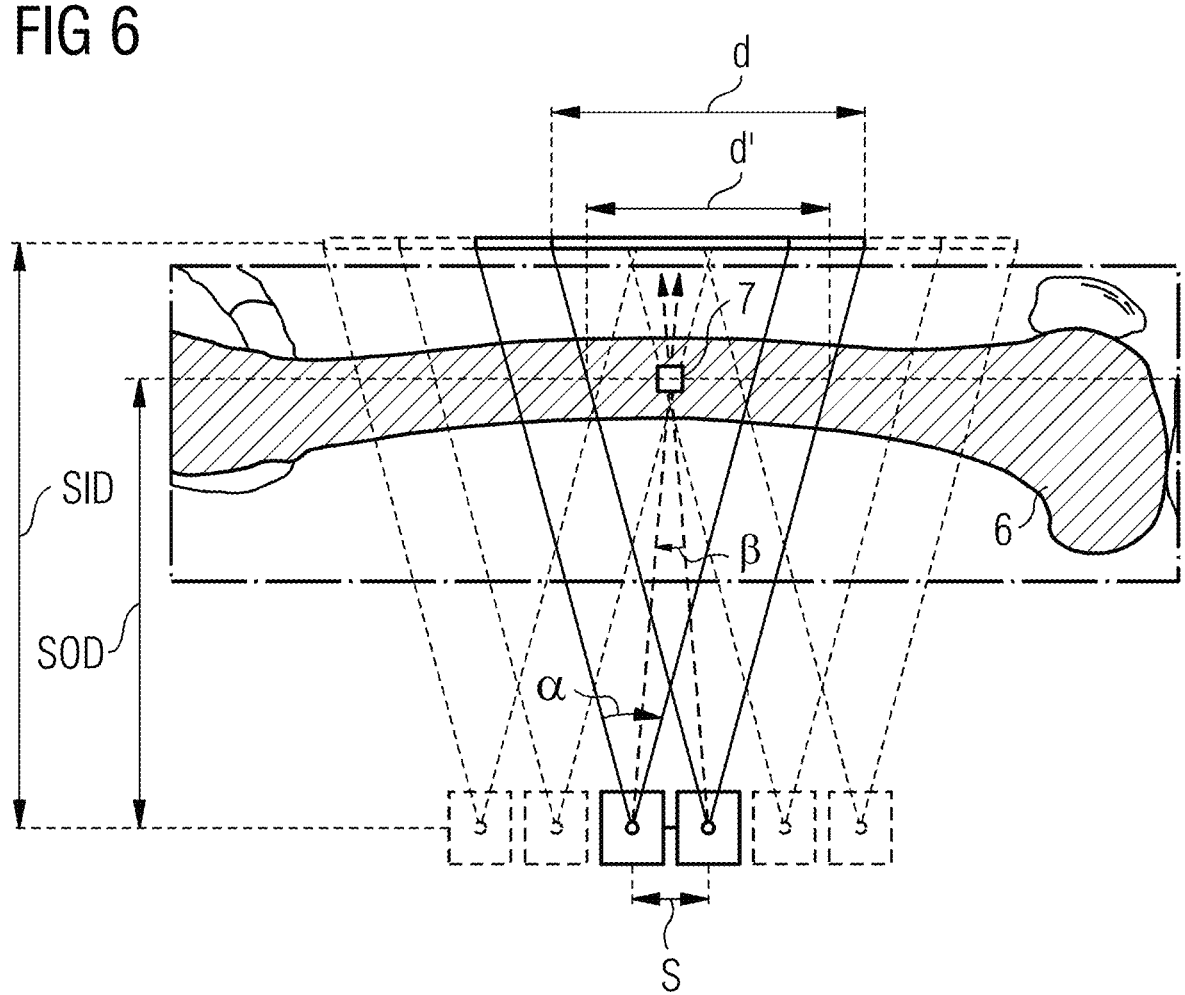
FIG. 6 shows a further view of the recording geometry according to FIG. 4.

In order to obtain depth information from two-dimensional x-ray images, the relevant anatomical positions are to be shown on at least two x-ray images. Consequently, the source distance s between two x-ray recordings are to be less than or equal to half of the detectable object width d' (see FIG. 6). In this case, the angle β between two projection directions with $$\beta \approx \frac{1}{2}$$

may be approached, where α corresponds to the opening angle of the x-ray source, and tan α=d/SID also applies.

The accuracy of the antitorsion angle determination depends significantly on how precisely 3D information may be determined from the x-ray images. An erroneous displacement Δ within the image plane with an effect of Δ/tan β is included in the estimation of the distance between the x-ray source and examination object (SOD). Therefore, with small opening angles, care is to be taken to provide that the angle β is maximized in order to improve the accuracy of the antitorsion angle determination.

With a source distance between the recordings of $$s(n) = \frac{1^n}{2} d',$$

the angle β between the projection directions corresponds to $$\beta(n) \approx \alpha\left(1 - \frac{1^n}{2}\right)$$

where n is the number of projection directions per spatial point. In other words, the maximum angle between the projections approaches α with an increasing n. With an adequate SNR of the x-ray images, n>3 is not necessarily useful for the determination of the antitorsion angle since the increase in β is still only small $\beta(3) \approx 0.9 \cdot \alpha$.

According to a further embodiment, the distance between two images of the plurality of partially spatially overlapping images differs as a function of a recording position along the elongated bone system. Provision may be made in the case of a femur, for example, for the distance in the central region of the femoral shaft to be higher and for a lower image quality thus to be achievable there. This adaptive sampling may be carried out in order to save on dosages. No anatomical structures that are relevant for determining the antitorsion angle are located in the region of the shaft. The distance between the x-ray images may be reduced to s(1)=1/2 d'. With other elongated bone systems, relevant regions may likewise be recorded with a particularly high quality (e.g., small distance), and less relevant regions may be recorded with a lower quality (e.g., greater distance).

For further dose reduction, the regions that do not belong to the femur may be blended out by a collimator.

Figure 7:
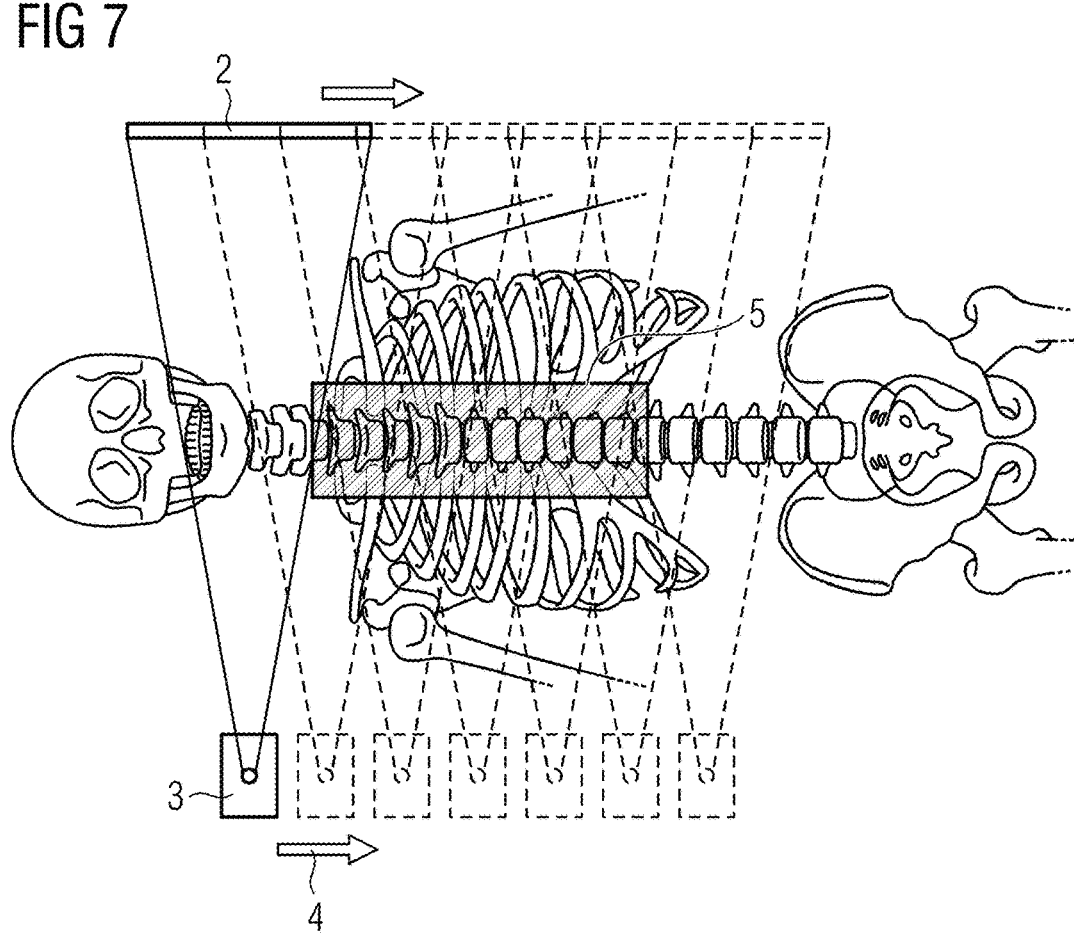
FIG. 7 shows one embodiment of a recording system for recording a plurality of partially spatially overlapping images for the purpose of displaying a spinal column.

A representation of the spinal column is shown in FIG. 7 as a further application example. A large part 5 of a spinal column may be shown by the method, and an angle between two vertebral bodies may be determined. On account of the significant overlapping of the shoulder region in the cervicothoracic transition, a sufficiently accurate display of a repositioning result during an OP of the spinal column is only possible with 3D imaging. With the known 3D scan, the x-ray apparatus is to move around the patient. The method of one or more of the present embodiments allows for easy inspection of the repositioning result by mapping the spinal column alignment in the sagittal plane. The method allows for an exact mapping of a slice present in the depth irrespective of overlapping structures such as, for example, the shoulders. Compared with the known 3D scan, the technology is faster, may be integrated better on account of absent orbital rotation, and requires less radiation exposure. If necessary, the entire spinal column may be mapped together. By selecting the correct slice (e.g., slice position and slice thickness), the spinal column may be shown isolated from overlapping objects (e.g., the shoulder region).

Figure 8:
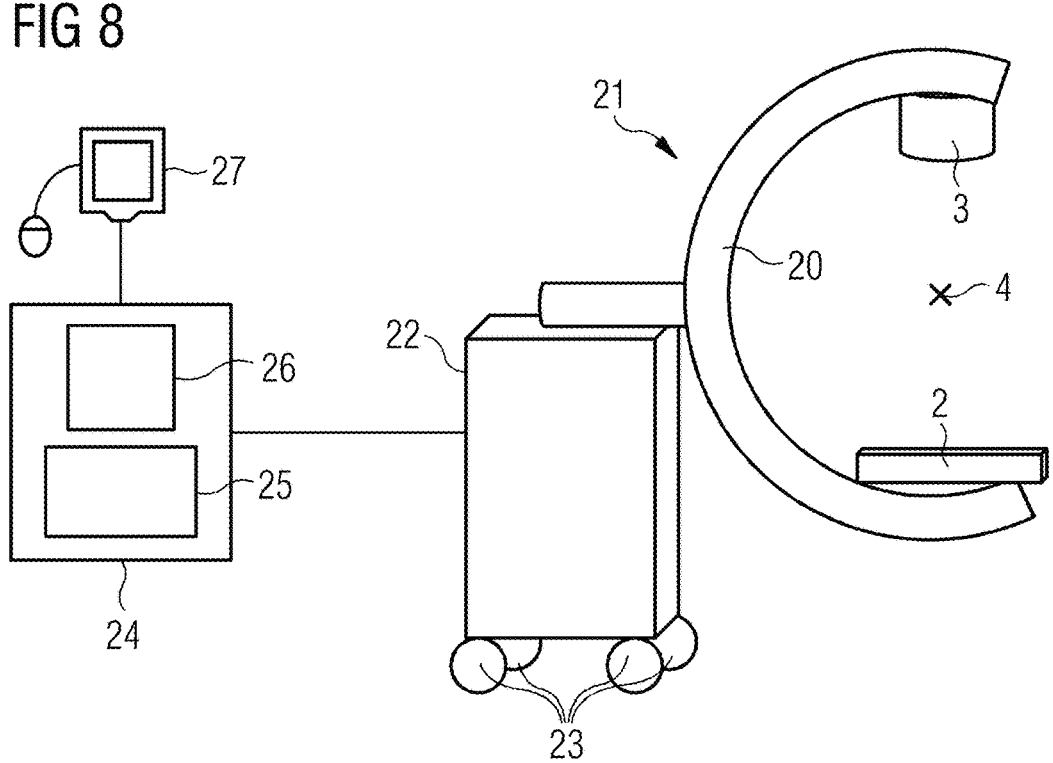
FIG. 8 shows one embodiment of a mobile C-arm x-ray device.

A mobile C-arm x-ray device 21 suited hereto is shown in FIG. 8. The mobile C-arm x-ray device 21 has a C-arm 20 that holds an x-ray source 3 and an x-ray detector 2. These form the recording system. The mobile C-arm x-ray system 21 has a trolley 22 that may be moved on rollers 23 and on which the C-arm 20 is arranged. The rollers 23 may be controlled and may be moved in a motorized manner (e.g., with a defined speed in a defined direction). The C-arm x-ray device 21 is controlled by a system controller 24. This may control, for example, a recording of a plurality of partially spatially overlapping x-ray images (e.g., tomosynthesis image data), while the mobile C-arm x-ray device 21 moves in a defined translational movement by the trolley 22. Moreover, the C-arm x-ray system has an image processing unit 25 for processing x-ray images and a calculation unit 26 for reconstructing slice images from the plurality of x-ray images and for determining the alignment angle from the slice images. Such a C-arm x-ray device 21 may be used in a sterile environment and during a surgical intervention.

The elongated bone system (e.g., femur) is arranged as close as is compatible with patient safety on the x-ray detector 2.

Figure 9:
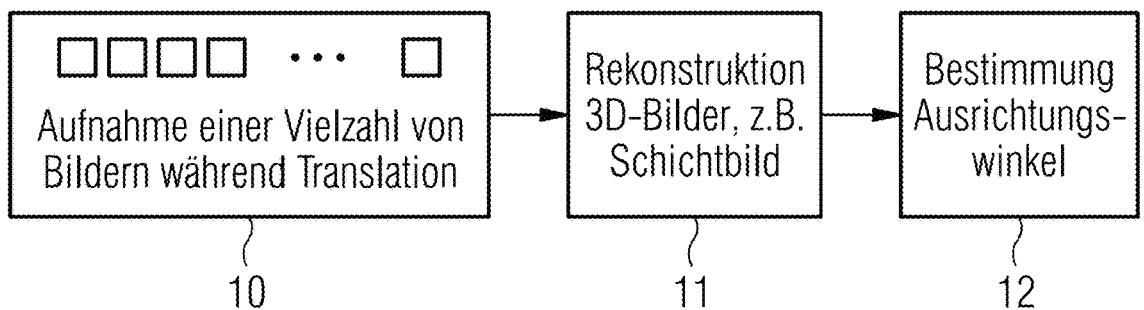
FIG. 9 shows a series of acts of one embodiment of a method.

FIG. 9 shows a sequence of acts of the method according to one or more of the present embodiments. In act 10, a plurality of partially spatially overlapping x-ray images are recorded, while the recording system (e.g., x-ray source and x-ray detector or C-arm holding the same) of the, for example, mobile C-arm x-ray device 21 is moved in a translational movement in the direction of or parallel to the longitudinal axis of the elongated bone system (e.g., femur or spinal column). In the case of the mobile C-arm x-ray device, the complete C-arm x-ray device moves forward on the trolley by the automatically controlled rollers in a defined translational movement such that the source distance s between each two images is less than or equal to half of the detector width of the x-ray detector. On account of the x-ray source-x-ray detector geometry (e.g., expanding x-ray beam), in such cases, the spatial points 7 passed over completely are shown in the plurality of x-ray images from different projection directions. It is accordingly advantageous to record the respective individual x-ray images in as short a time as possible (e.g., in less than 5 ms per x-ray image), so that as little smearing as possible results.

Alternatively, a non-mobile C-arm x-ray device may also be moved on rails, or only the recording system (e.g., C-arm) of a fixedly installed x-ray device may be moved.

In act 11, a three-dimensional slice image of the bone parts of the elongated bone system (e.g., the entire femur of a patient) is reconstructed from the recorded partially spatially overlapping x-ray images, for example. Alternatively, only 3D partial images or cutouts from images may also be reconstructed (e.g., only the femoral head and/or the femoral condyle). In act 12, an alignment angle between the at least two bone parts is determined or estimated at least partially based on the reconstructed slice image/images or the partial images or the projection images. Since a complete slice image of the entire elongated bone system may be produced by the tomosynthesis method, the geometric relations of the bone system may be easily derived from this one volume image (e.g., by applying straight lines and tangents to the relevant structures and/or using segmentations and/or image recognition algorithms).

The method of one or more of the present embodiments allows the antitorsion angle to be determined during a surgical intervention (e.g., before the femoral nail is locked). The method is characterized by a simple workflow within a sterile environment, a freely definable field of view along the direction of movement, and resulting slice images for determining, for example, the antitorsion angle. By determining the antitorsion angle, the distal end and the proximal end of the femur may be aligned more precisely with respect to one another. This results in fewer complications and complaints from the patient.

The method of one or more of the present embodiments is also advantageous in that on account of the translational movement, the workflow for the image acquisition is very simple. The complexity for the user (e.g., a physician carrying out a surgical intervention) is reduced since the physician is able to quantify the alignment angle (e.g., antitorsion angle) based on a complete volume and does not require two or more volume images produced independently of one another for this purpose. In addition, the applied radiation dose is significantly lower for a tomosynthesis scan than, for example, for two 3D recordings.

Figure 10:
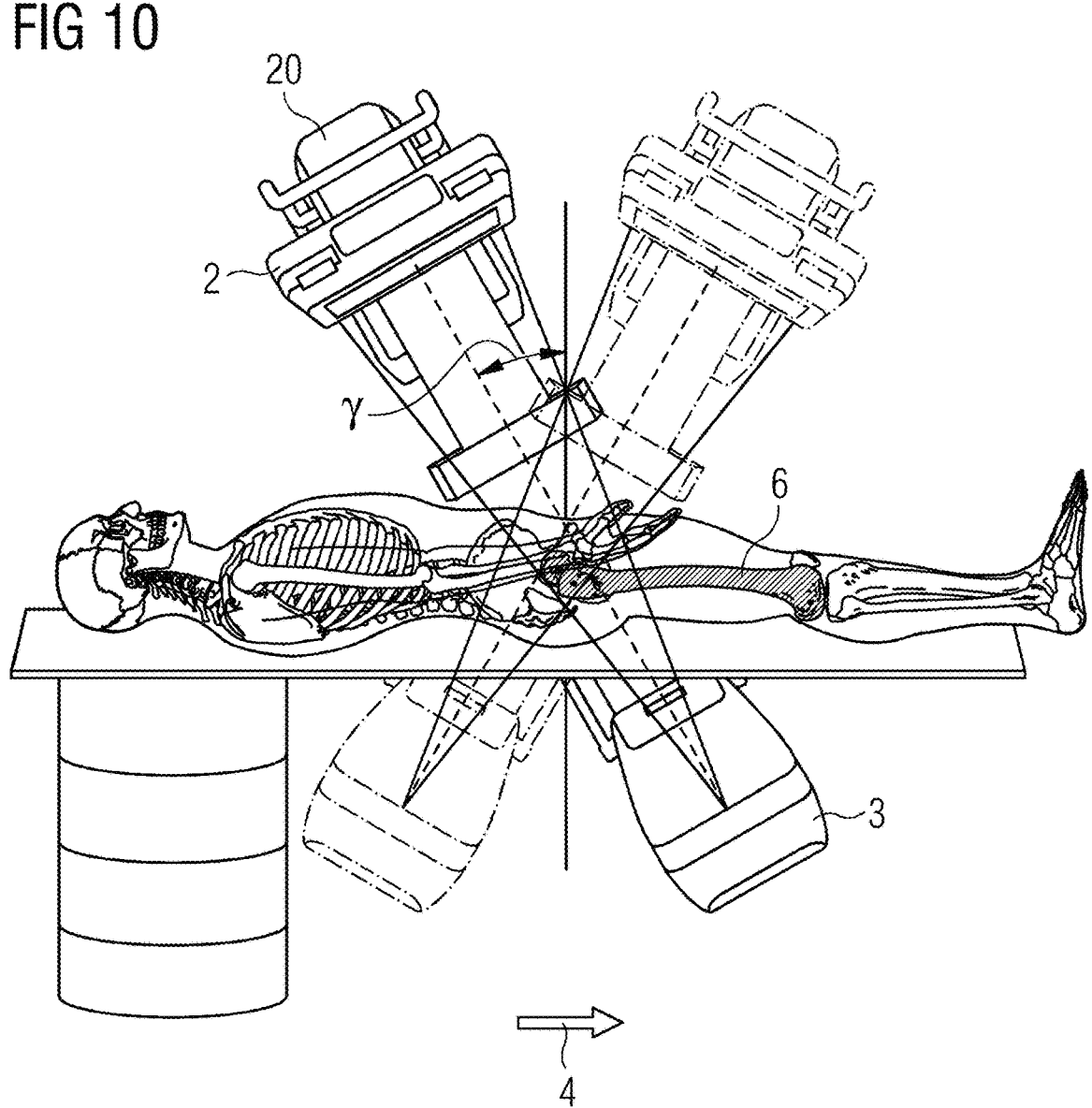
FIG. 10 shows one embodiment of a recording system with simultaneous translational and rotational movements.

A method is shown as a further exemplary embodiment in FIG. 10, in which in addition to translation a rotation of the C-arm is also carried out in order to determine an antitorsion angle. The workflow associated therewith is described below. The leg of the patient should not be moved during the entire workflow.

In a first part of the workflow, the orientation of the distal end of the femur is sought. The C-arm is arranged laterally (not shown), and a manual attempt is made per fluoroscopy to find a projection view, in which the central and the lateral condyle are arranged one behind the other along the x-ray beam and form a shared lower edge. The lower edge is then determined manually. The orientation and the height of the distal end of the femur or femoral condyle tangent are calculated herefrom.

The second and third part of the workflow are formed by an embodiment of the method.

The C-arm 20 is positioned in the second part of the workflow such that the C-arm 20 carries out a translation in the direction 4 along the femur 6 (e.g., including femoral head and large trochanter). The C-arm 20 is tilted about an angle of rotation γ (e.g., about −30° or as far as possible without colliding with the patient). While recording the plurality of projection images at a high frequency, the C-arm 20 is translated in the direction 4 of the axis of the elongated femur 6 and is rotated at the same time in the process (e.g., between the angles of rotation of +30° and −30°; over an angular increment of 60°) or between the maximum and the minimum possible angles of rotation γ (e.g., this may also change during the translation, the angular increment, fluctuate between 60° and 78°). The relation between rotation and translation is calculated or detected. For example, the femoral head and the large trochanter are scanned such that the entire femur may also be scanned.

The reconstruction and calculation of the antitorsion angle is carried out in the third part of the workflow. A 3D partial image of the surface of the femoral head and of the large trochanter is reconstructed based on the plurality of recorded projection images. The orientation of the femoral neck axis is determined based on this image data. The antitorsion angle is then produced from the difference between the orientations of the femoral neck axis and the previously determined femoral condyle tangent.

The present embodiments include a method for determining an alignment between at least two bone parts of an elongated bone system of a patient. The method includes recording a plurality of partially spatially overlapping projection images by a recording system of an x-ray device (e.g., a mobile x-ray device) during a translational movement of the x-ray device or of the recording system in a direction of or parallel to a longitudinal axis of the bone system. Tomosynthesis image data (e.g., slice images), of the bone parts is reconstructed from the recorded projection images, and an alignment angle is determined or estimated between the at least two bone parts at least partially based on the reconstructed tomosynthesis image data and/or the projection images.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining an alignment between at least two bone parts of an elongated bone system of a patient, the method comprising:
   recording, by a recording system of an x-ray device, a plurality of partially spatially overlapping projection images during a translational movement of the x-ray device or the recording system in a direction of or parallel to a longitudinal axis of the elongated bone system;
   reconstructing tomosynthesis image data of the at least two bone parts from the plurality of recorded partially spatially overlapping projection images; and
   determining or estimating an alignment angle between the at least two bone parts at least partially based on the reconstructed tomosynthesis image data, the plurality of recorded partially spatially overlapping projection images, or the reconstructed tomosynthesis image data and the plurality of recorded partially spatially overlapping projection images.

2. The method of claim 1, wherein the x-ray device is a mobile x-ray device.

3. The method of claim 2, wherein the mobile x-ray device is a mobile C-arm x-ray device.

4. The method of claim 1, wherein the tomosynthesis image data comprises slice images.

5. The method of claim 1, wherein a rotational movement of the recording system is carried out during the recording and the translational movement of the x-ray device.

6. The method of claim 1, wherein the determining or the estimating of the alignment angle between the at least two bone parts comprises determining or estimating the alignment angle between the at least two bone parts based exclusively on reconstructed tomosynthesis image data.

7. The method of claim 1, wherein further projection images are used in the determining or the estimating of the alignment angle between the at least two bone parts.

8. The method of claim 1, wherein a distance between two images of the plurality of partially spatially overlapping projection images is constant and less than or equal to half of an object width that is detectable by an opening angle of an x-ray source of the recording system.

9. The method of claim 1, wherein a distance between two images of the plurality of partially spatially overlapping projection images differs as a function of a recording position along the elongated bone system.

10. The method of claim 1, wherein the elongated bone system is formed of a femur and the alignment angle of an antitorsion angle.

11. The method of claim 1, wherein the elongated bone system is formed of a spinal column segment, and the alignment angle is formed of an angle between two vertebral bodies.

12. The method of claim 1, wherein the translational movement is carried out by automatically controlled rollers of the x-ray device along a floor.

13. The method of claim 1, wherein the translational movement is carried out along at least one rail.

14. An x-ray recording device for determining an alignment between at least two bone parts of an elongated bone system of a patient, the x-ray recording device comprising:
   a mobile C-arm x-ray device comprising:
      a recording system held on a C-arm, the recording system comprising an x-ray source and an x-ray detector;
   a system controller configured to control a recording of a plurality of partially spatially overlapping projection images by the recording system during a translational movement of the mobile C-arm x-ray device; and
   an image processor and a calculator configured to reconstruct tomosynthesis image data and determine an alignment angle.

15. The x-ray recording device of claim 14, wherein the tomosynthesis image data comprises slice images.

16. The x-ray recording device of claim 14, wherein the mobile C-arm x-ray device further comprises a trolley that is automatically movable on rollers, the C-arm being arranged on the trolley.

17. The x-ray recording device of claim 15, wherein the mobile C-arm x-ray device further comprises a trolley that is automatically movable on rollers, the C-arm being arranged on the trolley.

18. The method of claim 2, wherein the translational movement is carried out by automatically controlled rollers of the mobile x-ray device along a floor.

19. The method of claim 18, wherein the mobile x-ray device is a mobile C-arm x-ray device.

20. The method of claim 5, wherein the translational movement is carried out along at least one rail.

* * * * *